United States Patent
Park et al.

(10) Patent No.: US 12,036,060 B2
(45) Date of Patent: Jul. 16, 2024

(54) ARTIFICIAL INTELLIGENCE-BASED ORAL CT AUTOMATIC COLOR CONVERSION DEVICE AND METHOD FOR DRIVING SAME

(71) Applicants: MEGAGEN IMPLANT CO., LTD., Daegu (KR); KYUNGPOOK NATIONAL UNIVERSITY HOSPITAL, Daegu (KR); Kyungpook National University Industry-Academic Cooperation Foundation, Daegu (KR)

(72) Inventors: Kwang Bum Park, Daegu (KR); Keun Oh Park, Daegu (KR); Tae Gyoun Lee, Daegu (KR); Sung Moon Jeong, Daegu (KR); Dong Won Woo, Daegu (KR)

(73) Assignees: MEGAGEN IMPLANT CO., LTD. (KR); KYUNGPOOK NATIONAL UNIVERSITY HOSPITAL (KR); KYUNGPOOK NATIONAL UNIVERSITY INDUSTRY-ACADEMIC COOPERATION FOUNDATION (KR)

( * ) Notice: Subject to any disclaimer, the term of this patent is extended or adjusted under 35 U.S.C. 154(b) by 395 days.

(21) Appl. No.: 17/600,092

(22) PCT Filed: Oct. 8, 2020

(86) PCT No.: PCT/KR2020/013738
§ 371 (c)(1),
(2) Date: Sep. 29, 2021

(87) PCT Pub. No.: WO2021/132856
PCT Pub. Date: Jul. 1, 2021

(65) Prior Publication Data
US 2022/0183645 A1 Jun. 16, 2022

(30) Foreign Application Priority Data
Dec. 23, 2019 (KR) .......................... 10-2019-0172902

(51) Int. Cl.
*G06K 9/00* (2022.01)
*A61B 6/00* (2006.01)
(Continued)

(52) U.S. Cl.
CPC ............ *A61B 6/5217* (2013.01); *A61B 6/032* (2013.01); *A61B 6/51* (2024.01); *A61B 6/5205* (2013.01);
(Continued)

(58) Field of Classification Search
CPC .................................... A61B 6/14; G06T 7/00
See application file for complete search history.

(56) References Cited

U.S. PATENT DOCUMENTS

| 10,580,181 B2 * | 3/2020 | Shen | G06T 7/0012 |
| 2008/0058593 A1 * | 3/2008 | Gu | G06T 5/40 |
| | | | 600/109 |

(Continued)

FOREIGN PATENT DOCUMENTS

| CN | 202920375 U | 5/2013 |
| KR | 20120092451 A | 8/2012 |

(Continued)

OTHER PUBLICATIONS

Three-dimensional reconstruction of teeth and jaws based on segmentation of CT images using watershed transformation, S S Naumovich et al., Dentomaxillofacial Radiology, 2015, pp. 1-6 (Year: 2015).*

(Continued)

*Primary Examiner* — Jayesh A Patel
(74) *Attorney, Agent, or Firm* — Renaissance IP Law Group LLP (57) ABSTRACT

The present disclosure relates to an artificial intelligence-based oral CT automatic color conversion device and a method for driving same. The artificial intelligence-based
(Continued)

oral CT automatic color conversion device according to an embodiment of the present invention comprises: a storage unit which stores a color conversion image related to the bone density of an alveolar bone, which is previously prepared by a user; and a control unit which, when an oral CT input image of a patient is received, converts color of the received oral CT input image on the basis of a predetermined parameter value, and adjusts the predetermined parameter value by using an error value resulting from the converted oral CT input image and the (pre)stored color conversion image to automatically convert the color of an oral CT input image to be input later.

12 Claims, 5 Drawing Sheets

(51) Int. Cl.
 *A61B 6/03* (2006.01)
 *A61B 6/51* (2024.01)
 *A61B 34/10* (2016.01)
 *G06T 7/00* (2017.01)

(52) U.S. Cl.
 CPC .............. *A61B 6/5294* (2013.01); *A61B 6/54* (2013.01); *A61B 34/10* (2016.02); *G06T 7/00* (2013.01); *A61B 2034/105* (2016.02)

(56) References Cited

U.S. PATENT DOCUMENTS

| | | | |
|---|---|---|---|
| 2009/0042167 A1 | 2/2009 | Zel | |
| 2016/0157967 A1* | 6/2016 | Kim | A61C 8/005 433/201.1 |
| 2017/0086773 A1* | 3/2017 | Kamiya | A61B 6/502 |
| 2020/0184639 A1 | 6/2020 | Park et al. | |

FOREIGN PATENT DOCUMENTS

| | | | | |
|---|---|---|---|---|
| KR | 20120092451 A | * | 9/2012 | |
| KR | 101631256 B1 | * | 6/2016 | |
| KR | 101812484 B1 | | 12/2017 | |
| KR | 101981202 B1 | | 5/2019 | |
| KR | 101981202 B1 | * | 5/2019 | |
| KR | 20190105763 A | | 9/2019 | |
| KR | 20190105763 A | * | 10/2019 | |
| KR | 20190105763 A | * | 12/2019 | |
| TW | M445431 U | | 1/2013 | |
| TW | I397402 B | | 6/2013 | |
| WO | WO-2005011497 A1 | * | 2/2005 | ............... A61B 6/14 |
| WO | WO-2014207932 A1 | * | 12/2014 | ............... A61B 6/14 |
| WO | 2018066764 A1 | | 4/2018 | |
| WO | WO-2018066764 A1 | * | 4/2018 | ............... A61B 5/00 |
| WO | WO-2018127949 A1 | * | 7/2018 | ............... A61B 6/00 |

OTHER PUBLICATIONS

Alveolar bone changes in autogenous tooth transplantation, Aurasa Waikakul et al., 2011, pp. 1-7 (Year: 2011).*
Choice of diagnostic and therapeutic imaging in periodontics and implantology, Swarna Chakrapani et al., PubMed, 2013, pp. 711-718 (Year: 2013).*
Efficacy of digital intra-oral radiography in clinical dentistry, C. H. Versteeg, et al., Elsevier, 1997, pp. 215-224 (Year: 1997).*
Assessment of Alveolar Bone Mineral Density as a Predictor of Lumbar Fracture Probability, Yoshitomo Takaishi et al., Springer, 2013, pp. 487-502 (Year: 2013).*
Variations in bone density at dental implant sites in different regions of the jawbone, L.-J. Fuh et al., Journal of Oral Rehabilitation, 2010, pp. 346-351 (Year: 2010).*
International Search Report for PCT/KR2020/013738, mailed Jan. 15, 2021.

* cited by examiner

| Variables |
|---|
| M = [m_1, m_2, ..., m_N] (N-NUMBER OF HU MEAN VALUE) |
| R = [r_1, r_2, ..., r_N] (RANGE OF N-NUMBER OF HU VALUES) |
| Algorithm |
| for n=1:N<br><br>if I(r,c) > m_n-r_n & I(r,c) < m_n+r_n<br><br>I(r,c) = n<br><br>break<br><br>end<br><br>end |

ARTIFICIAL INTELLIGENCE-BASED ORAL CT AUTOMATIC COLOR CONVERSION DEVICE AND METHOD FOR DRIVING SAME

TECHNICAL FIELD

The present inventive concept relates to an artificial intelligence-based oral CT automatic color conversion device, and a driving method thereof, and more particularly, to an artificial intelligence-based oral CT automatic color conversion device, which may automatically convert colors on a screen according to a bone density of an alveolar bone, for example, when an implant is virtually placed in an alveolar bone, and a driving method thereof.

BACKGROUND ART

Dental implants originally mean substitutes for recovering when human body tissues is lost. However, in dentistry, dental implants refer to a series of treatments to transplant an artificial tooth. To replace a lost dental root (root), a fixture that is a dental root made of titanium, and the like that shows no rejection to human bodies is planted in an alveolar bone where a tooth is removed, and then an artificial tooth is fixed to restore the function of the tooth. For a general prosthesis or denture, as time passes, nearby teeth or bones are damaged, but the implant does not harm nearby teeth tissue and no cavity is generated while having the same function or shape as a natural tooth. Thus, it is advantageous to use the implant semi-permanently. Although there are various treatments according to the type of a fixture, generally, a general artificial tooth treatment (or referred to as an implant or an implant treatment) includes making a hole at an implant position using a certain drill, placing a fixture into an alveolar bone to be osseo-integrated to the bone, coupling an abutment to the fixture, and crowning the abutment with a final prosthesis, thereby completing the treatment.

The dental implant may facilitate restoration of a single missing tooth, enhance the function of a denture for partially toothless and fully toothless patients, improve an aesthetic aspect of dental prosthesis restoration, and furthermore distribute excessive stress applied to surrounding support bone tissues and stabilize a row of teeth. The dental implant may generally include a fixture placed as an artificial tooth root, an abutment coupled on the fixture, an abutment screw to fix the abutment to the fixture, and an artificial tooth coupled to the abutment. Before the abutment is coupled to the fixture, that is, during a period of osseo-integration of the fixture to the alveolar bone, a healing abutment may be coupled to the fixture and a coupling state is maintained.

The fixture, which is one of components of the dental implant, is a portion placed in a drill hole formed in the alveolar bone by using a drill, and functions as an artificial tooth root. Accordingly, the fixture is firmly placed in the alveolar bone. The placement of an implant varies much patient to patient because the placement position of an implant, and the like, is determined by various factors such as the state of a patient's tooth, the position of a tooth needing an implant treatment, the state of a patient's alveolar bone, and the like. In particular, the bone density of an alveolar bone is very important factor for placement of an implant, and the placement position, depth, and direction of an implant is determined according to the state of a patient's bone density, which is carefully determined considering the characteristics of a patient.

As described above, as the placement of an implant differs much for each patient, an image generation system for implant diagnosis to assist a doctor to accurately recognize such a difference has been developed. According to an image generation system for implant diagnosis according to the related art, an oral region of a patient is visually expressed by using a computed tomography (CT), and the like to assist a simulated treatment, and the like. However, it is a problem that an indication on the bone density of an alveolar bone that is very important in determining the placement position of an implant, and depth and direction is inaccurate and also provided in a state that a doctor is not able to recognize.

In particular, the image generation system for implant diagnosis according to the related art indicates the bone density of an alveolar bone with achromatic contrast only so that it is difficult for a doctor to quickly recognize the bone density of an alveolar bone. Furthermore, an overall bone density of an alveolar bone only is indicated, but bone densities of virtual positions where implants are to be placed are not separately provided so that a doctor takes long time to recognize an optimal implant placement position.

DETAILED DESCRIPTION OF THE INVENTIVE CONCEPT

Technical Problem

The present inventive concept provides an artificial intelligence-based oral CT automatic color conversion device, which may automatically convert colors on a screen according to the density of an alveolar bone, for example, when an implant is virtually placed in the alveolar bone, and a driving method thereof.

Solution to Problem

According to an aspect of the inventive concept, an artificial intelligence-based oral CT automatic color conversion device includes a storage unit configured to store a color conversion image previously manufactured by a user in relation to a bone density of an alveolar bone, and a control unit configured to automatically convert a color of an oral cavity CT input image that is input later, by converting a color of an oral cavity CT input image of a person who receives a treatment when the oral cavity CT input image is received, based on a preset parameter value, and adjusting the preset parameter value with an error value generated from the converted oral cavity CT input image and the stored color conversion image.

The control unit may be further configured to distinguish an area based on a feature of extracting from the received oral cavity CT input image and convert colors of the distinguished areas to be different from each other based on the preset parameter value.

The control unit may be further configured to calculate an error value after performing image preprocessing with a morphology operation on each of the converted oral cavity CT input image and the stored color conversion image.

The control unit may be further configured to convert the oral cavity CT input image based on an action selected by the user from among a plurality of actions used to adjust the preset parameter value.

The control unit may be further configured to use a pixel value of the oral cavity CT input image, as the parameter value, by quantizing the pixel value of the oral cavity CT input image into a plurality of colors different from each other.

When the user places a virtual implant in the alveolar bone on the received oral cavity CT input image of a person who receives a treatment, the control unit may automatically convert a color based on an action of placing the virtual implant in the alveolar bone and a bone density of the alveolar bone and visualize and display the converted oral cavity CT input image on a screen.

According to an aspect of the present inventive concept, a method of driving an artificial intelligence-based oral CT automatic color conversion device includes storing a color conversion image that is previously manufactured by a user, in a storage unit, in relation to a bone density of an alveolar bone, and when an oral cavity CT input image of a person who receives a treatment is received, automatically converting, by a control unit, a color of an oral cavity CT input image that is input later by converting the received oral cavity CT input image based on a preset parameter value, and adjusting the preset parameter value with an error value generated from the converted oral cavity CT input image and the stored color conversion image.

In the automatic color conversion, an area may be distinguished based on a feature of extracting from the received oral cavity CT input image and colors of the distinguished areas may be converted to be different from each other based on the preset parameter value.

In the automatic color conversion, an error value may be calculated after performing image preprocessing with a morphology operation on each of the converted oral cavity CT input image and the stored color conversion image.

In the automatic color conversion, the oral cavity CT input image may be converted by the control unit based on an action selected by the user from among a plurality of actions used to adjust the preset parameter value.

In the automatic color conversion, a pixel value of the oral cavity CT input image may be used as the parameter value, by quantizing the pixel value of the oral cavity CT input image into a plurality of colors different from each other.

In the automatic color conversion, when the user places a virtual implant in the alveolar bone on the received oral cavity CT input image of a person who receives a treatment, a color may be automatically converted based on an action of placing the virtual implant in the alveolar bone and a bone density of the alveolar bone and may be visualized and displayed on a screen.

Advantageous Effects

According to the present inventive concept, by employing image preprocessing, artificial intelligence training, and a visualization method thereof for auto color segmentation of a medical image area, indication accuracy of the bone density of an alveolar bone is increased so that a doctor may easily recognize the bone density of an alveolar bone. Furthermore, according to an embodiment, bone densities at virtual positions where implants are to be placed are visually and separately provided, so that an optimal implant placement by a doctor may be possible.

BRIEF DESCRIPTION OF THE DRAWINGS

Exemplary embodiments of the inventive concept will be more clearly understood from the following detailed description taken in conjunction with the accompanying drawings in which.

MODE OF THE INVENTIVE CONCEPT

Embodiments of the inventive concept are described in detail with reference to the accompanying drawings. However, the inventive concept is not limited thereto and it will be understood that various changes in form and details may be made therein without departing from the spirit and scope of the following claims. That is, descriptions on particular structures or functions may be presented merely for explaining embodiments of the inventive concept.

As the inventive concept allows for various changes and numerous embodiments, embodiments will be illustrated in the drawings and described in detail in the written description. However, this is not intended to limit the inventive concept to particular modes of practice, and it is to be appreciated that all changes, equivalents, and substitutes that do not depart from the spirit and technical scope of the inventive concept are encompassed in the inventive concept.

Terms such as "first" and "second" are used herein merely to describe a variety of constituent elements, but the constituent elements are not limited by the terms. Such terms are used only for the purpose of distinguishing one constituent element from another constituent element. For example, without departing from the right scope of the inventive concept, a first constituent element may be referred to as a second constituent element, and vice versa.

In the specification, when a constituent element "connects" or is "connected" to another constituent element, the constituent element contacts or is connected to the other constituent element directly or through at least one of other constituent elements. Conversely, when a constituent element is described to "directly connect" or to be "directly connected" to another constituent element, the constituent element should be construed to be directly connected to another constituent element without any other constituent element interposed therebetween. Other expressions, such as, "between" and "directly between," describing the relationship between the constituent elements, may be construed in the same manner.

Terms used in the specification are used for explaining a specific embodiment, not for limiting the inventive concept. Thus, an expression used in a singular form in the specification also includes the expression in its plural form unless clearly specified otherwise in context. Also, terms such as "include" or "comprise" may be construed to denote a certain characteristic, number, step, operation, constituent element, or a combination thereof, but may not be construed to exclude the existence of or a possibility of addition of one or more other characteristics, numbers, steps, operations, constituent elements, or combinations thereof.

Unless defined otherwise, all terms used herein including technical or scientific terms have the same meanings as those generally understood by those of ordinary skill in the art to which the inventive concept may pertain. The terms as those defined in generally used dictionaries are construed to have meanings matching that in the context of related technology and, unless clearly defined otherwise, are not construed to be ideally or excessively formal.

Hereinafter, the inventive concept will be described in detail by explaining preferred embodiments of the inventive concept with reference to the attached drawings. Like reference numerals in the drawings denote like elements.

Figure 1:
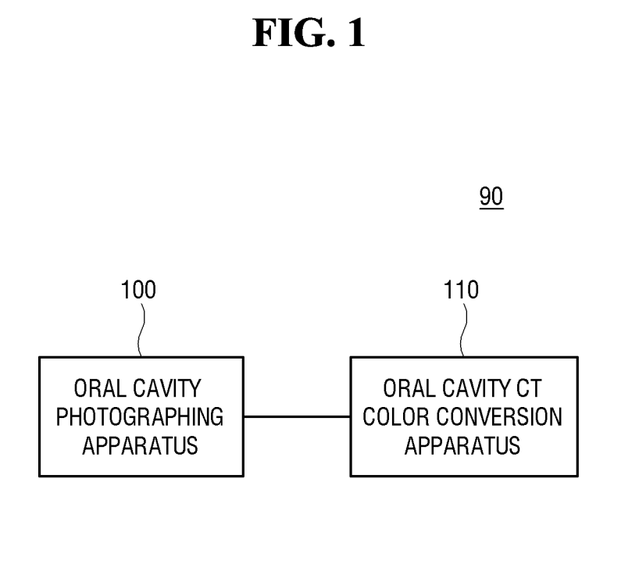
FIG. 1 illustrates an oral cavity CT color conversion system based on artificial intelligence, according to an embodiment of the present inventive concept.

FIG. 1 illustrates an oral cavity CT color conversion system based on artificial intelligence, according to an embodiment of the present inventive concept.

As illustrated in FIG. 1, an oral cavity CT color conversion system 90 based on artificial intelligence according to an embodiment of the present inventive concept may include a part or the whole of an oral cavity photographing apparatus 100 and an oral cavity CT color conversion apparatus 110.

The expression "include a part or the whole" may mean that the oral cavity CT color conversion system 90 based on artificial intelligence is configured by omitting some constituent elements such as the oral cavity photographing apparatus 100, and that some constituent elements such as the oral cavity photographing apparatus 100 is integrally formed with the oral cavity CT color conversion apparatus 110, and the like. To help sufficient understanding of the inventive concept, the expression is described as including the whole.

The oral cavity photographing apparatus 100 may include an apparatus for obtaining, for example, an image of an oral cavity of a patient, or a person who receives an implant treatment. For example, oral cavity photographing apparatus 100 may include various apparatuses such as a computed tomography (CT) scanner, a magnetic resonance imaging system, and the like. Additionally, any apparatus capable of obtaining an image of an alveolar bone, and the like in an oral cavity of a person who receives a treatment may be available. For example, while a CT scanner has a merit of accurately obtaining a bone shape, and the like of a person who receives a treatment, an image may be distorted by various prostheses and implants provided in the oral cavity of a person who receives a treatment.

Accordingly, the oral cavity photographing apparatus 100 according to an embodiment of the present inventive concept may further include a three-dimensional scanner that obtains an image by scanning a tooth plaster mold G. Image data by a scanner may include stereolithography (STL) data, and the STL data may have an ASCII or binary format, and may be data that expresses the surface of a three-dimensional object as a polygonised polygon to facilitate recognition of modeling data of a three-dimensional object in a 3D (dimension) program, in other types of 3D programs.

Furthermore, the oral cavity CT color conversion apparatus 110 may include various apparatuses such as desktop computers, laptop computers, tablet PCs, smartphones, smart TVs, and the like. The oral cavity CT color conversion apparatus 110 may prestore a color conversion image that is previously manufactured by an expert in relation to the color conversion image, that is, the bone density of an alveolar bone, which is configured such that a user may easily understand each area at a glance, for example, the color conversion image being manufactured by an expert having affluent prior knowledge in a relevant medical field, an image processing field, and the like, by sectioning an area of an alveolar bone and adjusting conversion parameters of an mean M and a range R of an HU value of a color for each area, by using a first photographed image and a second photographed image obtained by using the above CT scanner and a three-dimensional scanner, when an oral cavity CT input image of a user is received, convert a received CT input image based on a preset parameter value and determine a color conversion result state of a converted CT input image, and reflect an error generated in the converted CT input image and the prestored color conversion image to the preset parameter value, thereby automating the color conversion of a CT input image that is input later.

In other words, the oral cavity CT color conversion apparatus 110 may include a program assisting, for example, an implant placement treatment plan, and when an implant is virtually placed in an alveolar bone by executing the program, colors are changed on a screen according to the density of an alveolar bone, so that a doctor may perform an implant placement. In detail, in order to automatically perform color conversion of the density of an alveolar bone, the oral cavity CT color conversion apparatus 110 may prestore image data, that is, a color conversion image, related to the previously generated density of an alveolar bone and perform training of the image data through deep learning of artificial intelligence, and the like. In addition, the oral cavity CT color conversion apparatus 110 may pre-process each of prestored image data and newly input image data and then compare differences of the image data. When an error occurs as a result of the comparing, the state of preset parameters may be adjusted based on the comparison result and training may be performed. While performing training, automatic selection of parameters is possible and thus accuracy may be increased.

For example, in an embodiment of the inventive concept, when an oral cavity CT image is input as a parameter, an area is sectioned and the sectioned areas may be expressed with about N-number of colors. In a process of expressing colors, quantization is performed and thus the N-number of colors are determined and expressed. The "quantization" may be defined to be a method of dividing a range of a variable value into a limited number of small ranges or sections that do not overlap each other and representing each section with a designated value in the section or a method of dividing a range of a variable value into a limited number of partial ranges or sections that do not overlap each other. In this state, a conversion factor may be a parameter. The oral cavity CT color conversion apparatus 110 according to an embodiment of the present inventive concept may convert and output a newly or later input CT input image by adjusting the conversion factor, that is, a parameter, by reflecting an error based on the image data that is prestored, for example, image data that an expert in the corresponding field previously manually expressed and stored. Other detailed descriptions are discussed later.

As such, the oral cavity CT color conversion apparatus 110 may covert an oral cavity CT input image with a designated parameter value and then compare the image with prestored image data to determine whether an error has occurred. The process may be performed for each of various actions such as virtual implant placement, and by training the process, the color conversion of an oral cavity CT input image may be automated and simultaneously accuracy of the color conversion may be increased. For example, noise may be generated in a process of color conversion, and an irregular conversion result may be caused due to a limitation of a CT medical apparatus. Accordingly, considering the above, the oral cavity CT color conversion apparatus 110 performs the color conversion by adjusting the originally set parameter value, thereby increasing the accuracy of color conversion.

Figure 2:
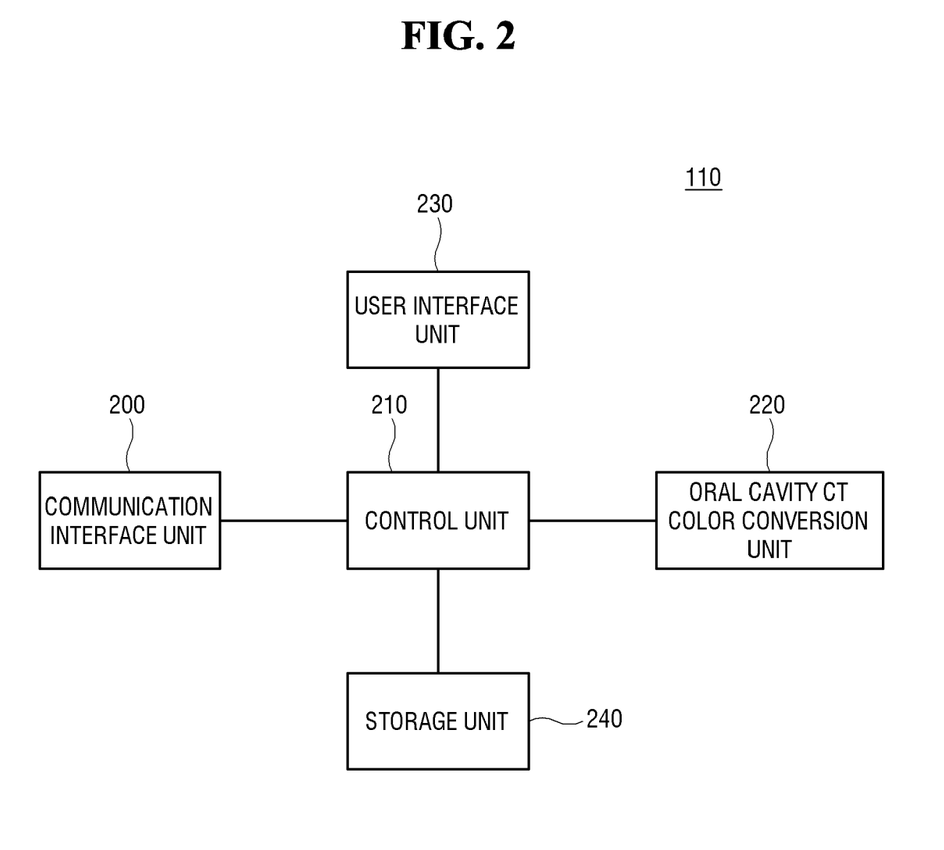
FIG. 2 is a block diagram of a detailed structure of an oral cavity CT color conversion apparatus of FIG. 1.

FIG. 2 is a block diagram of a detailed structure of the oral cavity CT color conversion apparatus of FIG. 1.

As illustrated in FIG. 2, the oral cavity CT color conversion apparatus 110 according to an embodiment of the present inventive concept may include a part or the whole of a communication interface unit 200, a control unit 210, an oral cavity CT color conversion unit 220, a user interface unit 230, and a storage unit 240, and may further include a display unit.

In this state, the expression "include a part or the whole" may mean that the oral cavity CT color conversion apparatus 110 is configured by omitting some constituent elements such as the storage unit 240, and that some constituent elements such as the oral cavity CT color conversion unit 220 is integrally formed with other constituent element such as the control unit 210, and the like. To help sufficient understanding of the inventive concept, the expression is described as including the whole.

The communication interface unit 200 may receive, for example, an oral cavity CT photography image obtained by photographing an oral cavity of a person who receives a treatment and provided from the oral cavity photographing apparatus 100 of FIG. 1 and transmit the received oral cavity CT photography image to the control unit 210. For example, when the communication interface unit 200 is integrally formed with the oral cavity photographing apparatus 100, for example, the oral cavity CT photography image may be received in an uncompressed state and provided to the control unit 210.

Accordingly, the communication interface unit 200 may receive a compressed image according to how a system designer configured the oral cavity CT color conversion apparatus 110 and perform an operation of decoding, and the like, or may not use the image. Accordingly, in an embodiment of the inventive concept, as various configurations are possible, the disclosure is not limited to any one specific form.

The control unit 210 may perform overall control operations of the communication interface unit 200, the oral cavity CT color conversion unit 220, the user interface unit 230, and the storage unit 240, which constitute the oral cavity CT color conversion apparatus 110 of FIG. 1. For example, the control unit 210 may store image data for training, that is, a previously generated color conversion image in the storage unit 240 so that the oral cavity CT color conversion unit 220 may perform a color conversion operation based on artificial intelligence and then provide the image data to the oral cavity CT color conversion unit 220. In this state, the training image data stored in the storage unit 240 may mean image data which is configured such that a user may easily understand each area at a glance as an expert having affluent prior knowledge manually adjusted conversion parameters of a mean M and a range R of an a pixel value or a mean M and a range R of an HU value of a color, to section an input oral cavity CT input image into a plurality of areas, for example, with respect to an alveolar bone and express the respective sectioned areas in different colors. Such data may be possibly received from an external medical organization, and the like for use. Collecting and using big data in related fields may be useful for deep learning of artificial intelligence. In other words, using much data may increase objectivity or accuracy of a result.

Furthermore, the control unit 210 may receive an action to virtually place an implant in an alveolar bone through the user interface unit 230. The control unit 210 may receive a user interface signal. The action may be one of various events extracted through deep learning. The control unit 210 may provide a received interface signal to the oral cavity CT color conversion unit 220, and provide an accordingly generated color change in an alveolar bone image to a display, and the like again. A color or an oral cavity CT input image converted according to an embodiment may be visualized and displayed on a screen of the display.

The oral cavity CT color conversion unit 220 may include a program to assist, for example, a dentist's implant placement treatment plan, and execute the program under the control of the control unit 210. When a CT input image of a person who receives a treatment is received through the communication interface unit 200, the oral cavity CT color conversion unit 220 may store the CT input image in the storage unit 240.

Furthermore, for example, when an action to place a virtual implant in an alveolar bone is received through the user interface unit 230, the oral cavity CT color conversion unit 220 is driven to apply the action to the CT input image stored in the storage unit 240. In the process, reference image data prestored in the storage unit 240, that is, the color conversion image that is previously generated and stored, may be referred to and trained. For example, the oral cavity CT color conversion unit 220 may perform a color conversion on the received oral cavity CT input image with respect to a designated area by using s designated parameter value. However, an irregular conversion result may be caused on the color-converted oral cavity CT input image due to noise and a limitation of a CT medical apparatus.

Accordingly, the oral cavity CT color conversion unit 220 modifies a designated parameter value by referring to and training image data that is converted as an expert having affluent prior knowledge in a relevant field manually operates the oral cavity CT photography image obtained by photographing oral cavities of a plurality of persons who receive treatments. Such a parameter value modification may be performed for each of various actions. Accordingly, the oral cavity CT color conversion unit 220 adjusts an error to increase the accuracy of a color conversion, and thus automatically color converted image data may be displayed on the display, and the like.

The user interface unit 230 may receive various commands of a user, for example, a dentist. The user interface unit 230 may mean, for example, a keyboard or a mouse for a computer. The user interface unit 230 may further include a display unit such as a monitor. For a display unit, when a touch panel is included, a screen touch may be possible so that a user command may be received.

For example, a dentist may obtain an oral cavity CT photography image of a person who receives a treatment, and then execute a program according to an embodiment of the present inventive concept and place a virtual implant in an alveolar bone on a display to check a color of the density of the alveolar bone. Accordingly, accuracy of an implant placement may be increased by determining a placement strength or an accurate position. To this end, the oral cavity CT color conversion unit 220 may use the image data generated by an expert through a conventional manual operation, and correct an error by comparing with the image data generated by the expert to correct noise or a limitation of a CT medical apparatus and also by performing training based on artificial intelligence in the process, thereby increasing accuracy.

The storage unit 240 may store, under the control of the control unit 210, various pieces of information and data. In this state, the information may mean an interface signal of a user, that is, a dentist, for placement, and the data may mean image data, and the like, of a photographed image, but an embodiment of the inventive concept is not particularly limited to the concept of the terms.

The storage unit 240 may store training data obtained by performing a color conversion through a manual operation on the oral cavity CT images obtained by an expert from a plurality of persons who receive treatments. The training data may be provided, under the control of the control unit 210, to the oral cavity CT color conversion unit 220.

Figure 3:
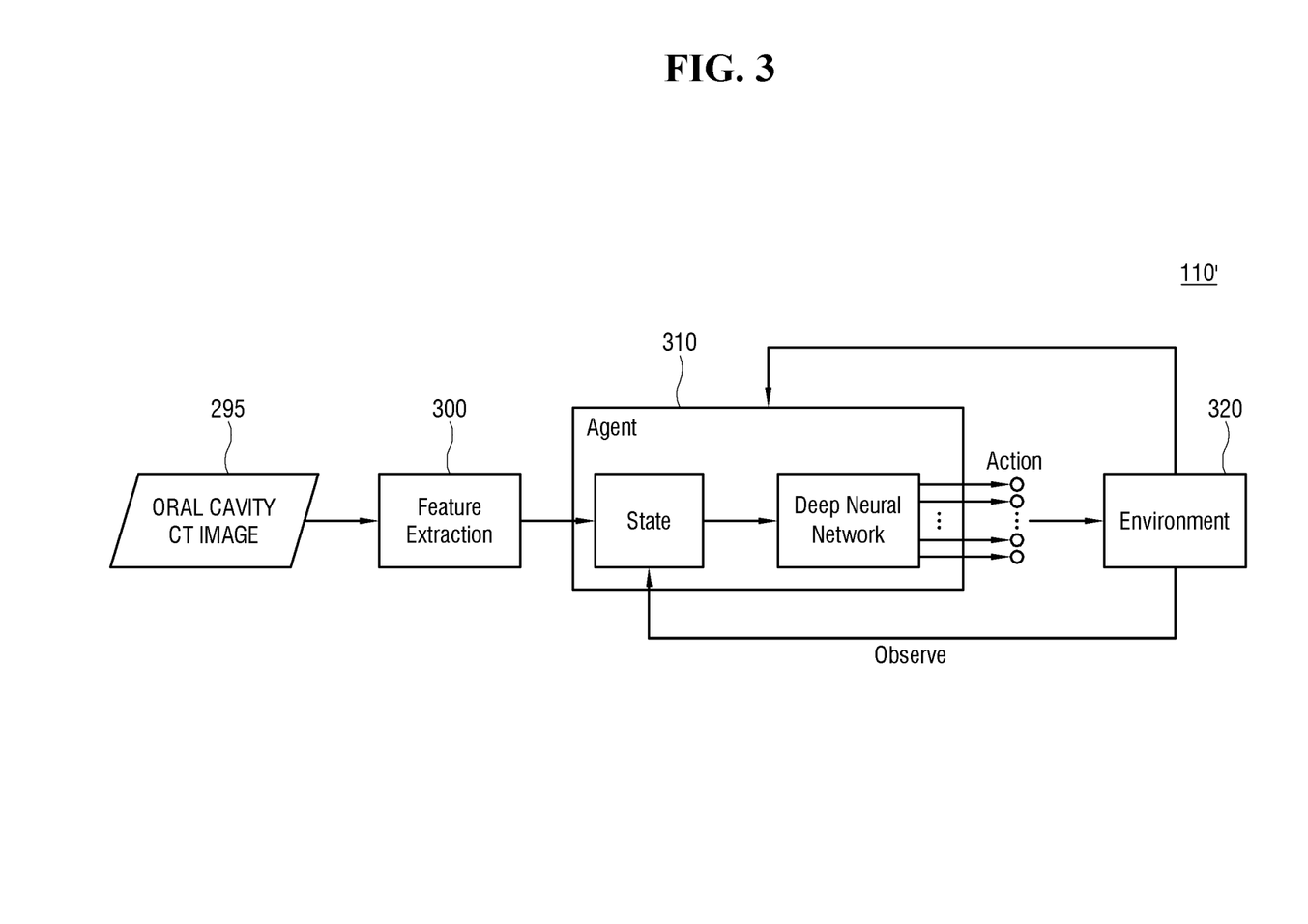
FIG. 3 is a block diagram of other detailed structure of the oral cavity CT color conversion apparatus of FIG. 1.
Figure 4:
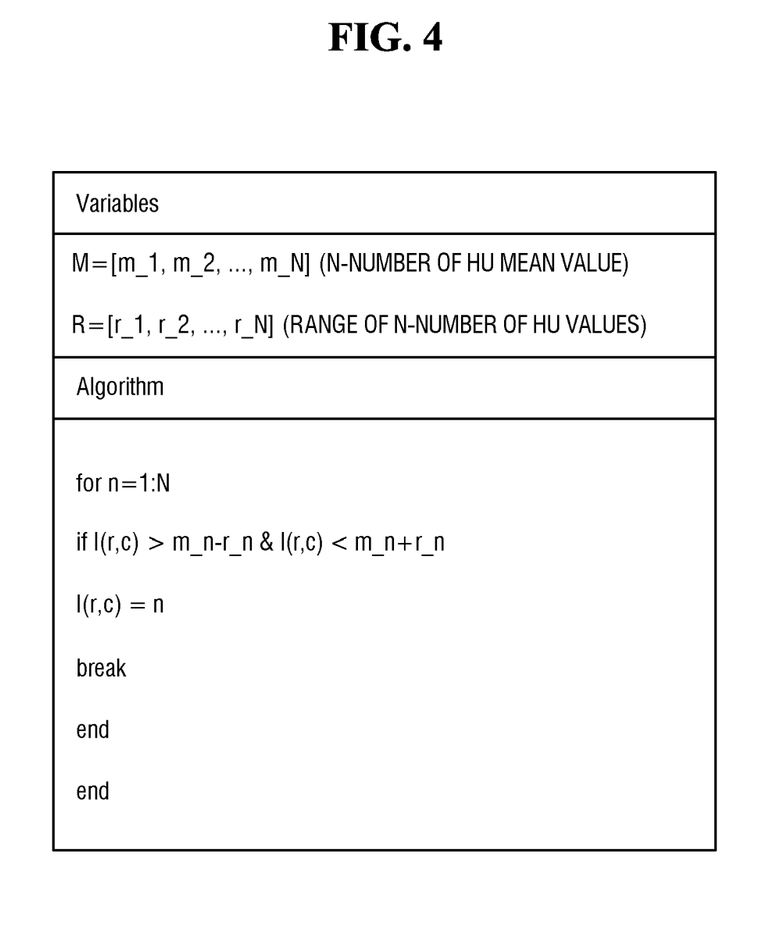
FIG. 4 illustrates N-number of color conversion methods.

FIG. 3 is a block diagram of other detailed structure of the oral cavity CT color conversion apparatus of FIG. 1. FIG. 4 illustrates N-number of color conversion methods.

As illustrated in FIG. 3, an oral cavity CT color conversion apparatus 110' according to another embodiment of the inventive concept may perform image preprocessing, artificial intelligence training, and a visualization operation for auto color segmentation of a medical image area, and to this end, may include a part or the whole of a feature extraction unit 300, an agent unit 310, and a color conversion unit 320.

In this state, the expression "include a part or the whole" may mean that the oral cavity CT color conversion apparatus 110 is configured by omitting some constituent elements such as the feature extraction unit 300, and that some constituent elements such as the color conversion unit 320 is integrally formed with other constituent element such as the agent unit 310, and the like. To help sufficient understanding of the inventive concept, the expression is described as including the whole. Furthermore, the above constituent elements may be configured with software S/W, hardware H/W, or a combination thereof.

The feature extraction unit 300 may extract a feature from an oral cavity CT image 295 that is input. For example, a CT image may be received in units of frames, or in units of macroblocks that are obtained by splitting a unit frame image into a plurality of blocks. Accordingly, the feature extraction unit 300 may extract a state(s) to be used for, for example, reinforcement learning, through the feature extraction. In detail, the feature extraction unit 300 may use various feature extraction algorithms to extract a state(s) to be used for reinforcement learning, from a CT input image. For example, various algorithms such as U-Net, AutoEncoder, a convolutional neural network (CNN), and the like, may be used.

The agent unit 310 may train an agent to have an appropriate color conversion by allowing a color conversion image generated based on a result of the reinforcement learning to pass through image preprocessing such as a morphology operation, and the like, and then defining a difference $E(i-i\_)^2$ between the color conversion image and a color conversion image manufactured by an expert having passed the same image preprocessing, to be an error, and defining a reciprocal of the error to be a reward of the reinforcement learning.

First, a process of generating image data in a manual method used by the agent unit 310 is briefly described. A feature of a medical image using CBCT, and the like has a different Hounsfield unit (HU) value for each area. HU values may have difference scales according to the physical properties of various areas, for example, a tooth, an alveolar bone, and the like, for CBCT scanning. Furthermore, as effective visualization of a medical image using CBCT, and the like is made, parameter based color split is possible. To convert (quantize) pixel values for each different area in different colors, N-number of colors may be determined, and N-number of HU mean values and ranges for quantization are manually adjusted by a user, and when an actual pixel value (HU) is included in N-number of different quantization areas, the pixel values for each different area is quantized with a representative color value, thereby obtaining a color number or a result. FIG. 4 illustrates N-number of color conversion methods.

In the manual method used to generate a previously generated color conversion image according to an embodiment, for splitting into different colors, an expert having affluent prior knowledge may adjust conversion parameters including mean M of HU value (the "HU mean value" in FIG. 4) and range R of HU values (the "range of HU values" in FIG. 4) a color to be expressed manually. Accordingly, a configuration which enables a user to understand each area at a glance is possible. The conversion (quantization) by filtering in units of pixel values (HU values) may cause an irregular color conversion result, in spite of the same area. In other words, the conversion image using a HU value, which is a conversion by linear filtering using the range of pixel values may cause an irregular conversion result, in spite of the same area, due to noise and a limitation of a CT medical apparatus. To address the problem, a regular color conversion result may be reconstructed through image processing technology such as a morphology operation, and the like, which is applied to the conversion image prepared by an expert.

Accordingly, in an embodiment of the inventive concept, to implement an expert-level automatic color conversion algorithm based on a reconstructed color conversion result, various parameters (M, R) and color conversion result state(s) used for a manual conversion is defined based on a reinforcement learning method, for example, a deep Q-network, and the like, and an action (a) to convert values of the parameters is defined so that an expert-level color conversion is automatically performed. A conversion image manufactured by an expert by a conventional manual method is modified to a regular color conversion image through image preprocessing such as a morphology operation, and the like image preprocessing, and the image is used as an output (target) data, which is reconstructed from a CT that is input data by using current parameters (M, R), and a difference between the reconstructed image and a result passing through image preprocessing such as a morphology operation, and the like, is defined to be an error, and a reciprocal of the error is sued as a reward of a deep Q-network (DQN) structure and thus training to convert a state of the parameter is performed. As the training proceeds, automatic selection of a parameter is converted similarly to an expert level.

The agent unit 310 according to an embodiment may reconstruct a color conversion image manufactured by an expert through a morphology operation, and the like based on an image preprocessing model for training data purification, in a regular color conversion result, to purify the training data, thereby increasing artificial intelligence training performance A parameter (p) is defined (N, m_n, m_r), which is necessary during an image conversion manually performed by an expert based on a DQN structure that is one of reinforcement learning models as a background model.

An action unit (not shown) may update a result of a color conversion based on a result of selection from among three result definitions of the reinforcement learning, for example, increase, decrease, and maintain, that is, 3*N-number of reinforcement learning results, to adjust N-number of conversion parameter (P) values.

The color conversion unit (environment) 320 may perform an operation of converting a color by using a parameter determined by the agent unit 310. For example, the color conversion unit 320 may convert a color based on a parameter with respect to the split areas of a CT input image.

Furthermore, the color conversion unit 320 may perform a feedback operation to the agent unit 310. The feedback operation may correspond to a reward operation in an embodiment. In this state, a reward is a reciprocal of a difference (mean square error) between a parameter changed from a determined action and an actual parameter, and may correspond to a reciprocal of a difference (pixel-wise crossentropy) between an image that is color converted by using a parameter determined from a determined action and then passed through image preprocessing such as morphology, and the like and a color conversion result manually manufactured by an expert through image preprocessing such as morphology, and the like.

The agent unit 310 may define a parameter p necessary for image conversion performed manually by an expert based on a DQN structure that is one of reinforcement learning models as a background model, and reconstruct the color conversion image manufactured by an expert through an image preprocessing model for training data purification, such as morphology operation, and the like, as a regular color conversion result, to purify training data so that artificial intelligence training performance is increased.

Figure 5:
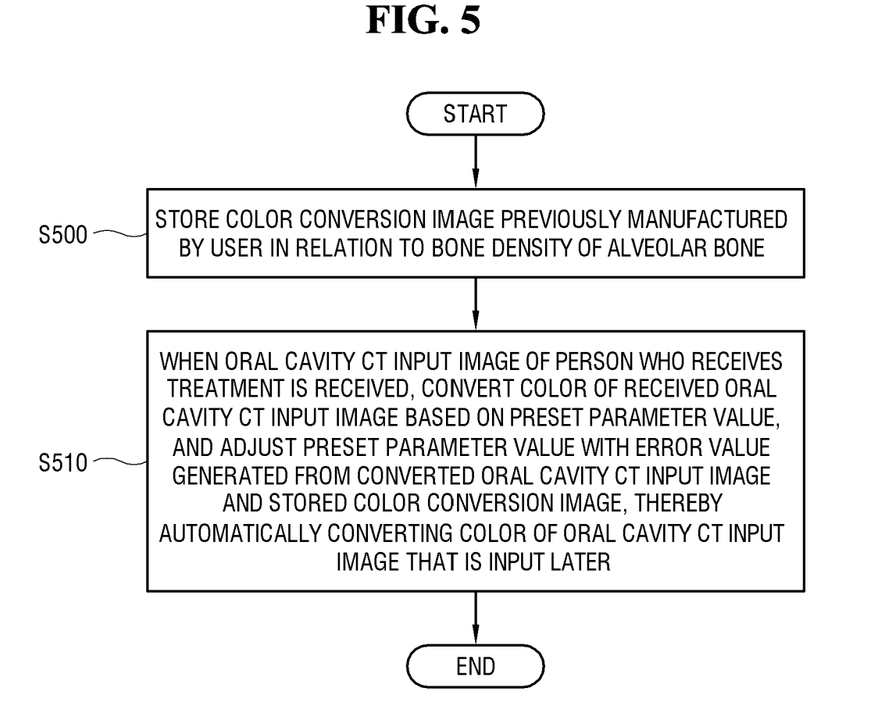
FIG. 5 is a flowchart of a driving process of the oral cavity CT color conversion apparatus of FIG. 1.

FIG. 5 is a flowchart of a driving process of the oral cavity CT color conversion apparatus of FIG. 1.

For convenience of explanation, referring to FIG. 5 with FIG. 1, the oral cavity CT color conversion apparatus 110 of FIG. 1 according to an embodiment of the present inventive concept stores a color conversion image previously manufactured by a user or an expert in relation to the bone density of an alveolar bone or a tooth, in a storage unit (S500). In this state, a previously manufactured color conversion image may be a reference or standard image used when an oral cavity CT image input by photographing an oral cavity of a person who receives a treatment is color converted.

Furthermore, when an oral cavity CT input image of a person who receives a treatment is received, the oral cavity CT color conversion apparatus 110 converts the received oral cavity CT input image based on a preset parameter value, and reflects an error generated from the converted oral cavity CT input image and a prestored color conversion image, in a preset parameter value, so that the color conversion of an oral cavity CT input image that is input later is automated (S510).

In addition to the above content, the oral cavity CT color conversion apparatus 110 of FIG. 1 may perform various operations, and as other detailed contents are sufficiently described above, redundant descriptions thereof are omitted.

Although it has been described in the above that all the components of an embodiment of the disclosure are coupled as a single unit or coupled to be operated as a single unit, the disclosure is not necessarily limited to such an embodiment. Namely, within the purpose of the disclosure, one or more components among the components may be selectively coupled to be operated as one or more units. Also, although each of the components may be implemented as an independent hardware, some or all of the components may be selectively combined with each other, so that they may be implemented as a computer program having one or more program modules for performing some or all of the functions combined in one or more hardware. Codes and code segments forming the computer program can be easily conceived by an ordinarily skilled person in the technical field of the disclosure. Such a computer program may implement the embodiments of the disclosure by being stored in a non-transitory computer-readable medium, and being read and executed by the computer.

The non-transitory readable recording medium is not a medium that stores data for a short moment, such as registers, cache, memory, and the like, but may mean a medium capable of storing data semi-permanently and being readable by a device. In detail, the above-described programs may be provided by being stored in a non-transitory readable recording medium such as CD, DVD, hard disk, Blu-ray disk, USB, memory card, ROM, and the like.

As such, while this disclosure has been particularly shown and described with reference to preferred embodiments thereof, it will be understood by those of ordinary skill in the art that various changes in form and details may be made therein without departing from the spirit and scope of the inventive concept as defined by the appended claims. The preferred embodiments should be considered in descriptive sense only and not for purposes of limitation. Therefore, the scope of the inventive concept is defined not by the detailed description of the inventive concept but by the appended claims, and all differences within the scope will be construed as being included in the inventive concept.

INDUSTRIAL APPLICABILITY

The present inventive concept may be used for artificial intelligence industry and a dental medical industry.

The invention claimed is:

1. An artificial intelligence-based oral CT automatic color conversion apparatus, the apparatus comprising:
   a storage unit configured to store a color conversion image previously manufactured by a user in relation to a bone density of an alveolar bone; and
   a control unit configured to automatically convert a color of an oral cavity CT input image that is input later, by converting a color of an oral cavity CT input image of a person who receives a treatment when the oral cavity CT input image is received, based on a preset parameter value, and adjusting the preset parameter value with an error value generated from the converted oral cavity CT input image and the stored color conversion image.

2. The apparatus of claim 1, wherein the control unit is further configured to distinguish an area based on a feature of extracting from the received oral cavity CT input image and convert colors of the distinguished areas to be different from each other based on the preset parameter value.

3. The apparatus of claim 1, wherein the control unit is further configured to calculate an error value after performing image preprocessing with a morphology operation on each of the converted oral cavity CT input image and the stored color conversion image.

4. The apparatus of claim 1, wherein the control unit is further configured to convert the oral cavity CT input image based on an action selected by the user from among a plurality of actions used to adjust the preset parameter value.

5. The apparatus of claim 1, wherein the control unit is further configured to use a pixel value of the oral cavity CT input image, as the parameter value, by quantizing the pixel value of the oral cavity CT input image into a plurality of colors different from each other.

6. The apparatus of claim 1, wherein, when the user places a virtual implant in the alveolar bone on the received oral cavity CT input image of a person who receives a treatment, the control unit automatically converts a color based on an action of placing the virtual implant in the alveolar bone and a bone density of the alveolar bone and visualizes and displays the converted oral cavity CT input image on a screen.

7. A method of driving an artificial intelligence-based oral CT automatic color conversion device, the method comprising:
   storing a color conversion image that is previously manufactured by a user, in a storage unit, in relation to a bone density of an alveolar bone; and
   when an oral cavity CT input image of a person who receives a treatment is received, automatically converting, by a control unit, a color of an oral cavity CT input image that is input later by converting the received oral cavity CT input image based on a preset parameter value, and adjusting the preset parameter value with an error value generated from the converted oral cavity CT input image and the stored color conversion image.

8. The method of claim 7, wherein, in the automatic color conversion, an area is distinguished based on a feature of extracting from the received oral cavity CT input image and colors of the distinguished areas are converted to be different from each other based on the preset parameter value.

9. The method of claim 7, wherein, in the automatic color conversion, an error value is calculated after performing image preprocessing with a morphology operation on each of the converted oral cavity CT input image and the stored color conversion image.

10. The method of claim 7, wherein, in the automatic color conversion, the oral cavity CT input image is converted by the control unit based on an action selected by the user from among a plurality of actions used to adjust the preset parameter value.

11. The method of claim 7, wherein, in the automatic color conversion, a pixel value of the oral cavity CT input image is used as the parameter value, by quantizing the pixel value of the oral cavity CT input image into a plurality of colors different from each other.

12. The method of claim 7, wherein, in the automatic color conversion, when the user places a virtual implant in the alveolar bone on the received oral cavity CT input image of a person who receives a treatment, a color is automatically converted based on an action of placing the virtual implant in the alveolar bone and a bone density of the alveolar bone and is visualized and displayed on a screen.

* * * * *